US00PP22703P2

(12) United States Plant Patent
Smith

(10) Patent No.: US PP22,703 P2
(45) Date of Patent: May 1, 2012

(54) *ASTER* PLANT NAMED 'SYNBUL HENFIRST'

(50) Latin Name: *Aster hybrida*
Varietal Denomination: Synbul Henfirst

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 22 days.

(21) Appl. No.: 12/925,474

(22) Filed: Oct. 22, 2010

(51) Int. Cl.
*A01H 5/00* (2006.01)

(52) U.S. Cl. ..... Plt./355

(58) Field of Classification Search ..... Plt./355
See application file for complete search history.

*Primary Examiner* — June Hwu
(74) *Attorney, Agent, or Firm* — Joshua L. Price

(57) ABSTRACT

A new *Aster* plant named 'Synbul Henfirst' particularly distinguished by the medium sized, long lasting, double-type inflorescences with violet ray floret color, dark yellow-green foliage, upright, freely branched and rounded plant habit, and a natural season flowering in early to mid September in the north.

1 Drawing Sheet

Latin name of the genus and species of the plant claimed: *Aster hybrida.*

Varietal denomination: 'Synbul Henfirst'.

BACKGROUND OF THE NEW PLANT

The present invention comprises a new *Aster*, botanically known as *Aster hybrida*, and hereinafter referred to by the variety name 'Synbul Henfirst'.

'Synbul Henfirst' is a product of a planned breeding program. The new cultivar has medium sized, long lasting, double-type inflorescences with violet ray floret color, dark yellow-green foliage, upright, freely branched and rounded plant habit, and a natural season flowering in early to mid September in the north.

'Synbul Henfirst' originates as a natural whole plant mutation of 'Synhen Thefirst', U.S. Ser. No. 12/925,435, and was discovered and selected by the inventor as a single flowering plant within a large population of the parent cultivar, grown massed in pots outdoors in a controlled breeding program in Alva, Fla. in April 2008. The parent cultivar 'Synhen Thefirst' has fewer ray florets with a lighter violet colored ray floret and a little lighter green foliage than of 'Synbul Henfirst'.

The first act of asexual reproduction of 'Synbul Henfirst' was accomplished when vegetative cuttings were propagated from the initial selection in June 2008 in a controlled environment in Alva, Fla.

BRIEF SUMMARY OF INVENTION

Horticultural examination of plants grown from cuttings of the plant initiated in June 2008, and continuing thereafter, has demonstrated that the combination of characteristics as herein disclosed for 'Synbul Henfirst' are firmly fixed and are retained through successive generations of asexual reproduction.

'Synbul Henfirst' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6775). 'Synbul Henfirst' has not been made publicly available more than one year prior to the filing of this application.

The following traits have been repeatedly observed and are determined to be basic characteristics of the new variety. The combination of these characteristics distinguishes this *Aster* as a new and distinct variety.

BRIEF DESCRIPTION OF THE PHOTOGRAPHS

The accompanying photographic drawing shows typical flower and foliage characteristics of 'Synbul Henfirst' with colors being as true as possible with an illustration of this type.

The photographic drawing shows 3 flowering potted plants of the new variety growing in the same pot and a close-up of the flowers.

DETAILED BOTANICAL DESCRIPTION

The plant descriptions, measurements and aforementioned photographs were taken in Gilroy, Calif. in May 2010 under natural light. These plants used in the photograph and descriptions were about 12 weeks old. Plants were grown in an 8 inch pot with 3 plants per pot.

Color references are made to The Royal Horticultural Society Colour Chart (R.H.S.) 2001.

TABLE 1

DIFFERENCES BETWEEN THE NEW VARIETY 'SYNBUL HENFIRST' AND A SIMILAR VARIETY: 'MILKA' (U.S. Plant Pat. No. 10,602)

| | 'Sybul Henfirst' | 'Milka' (U.S. Plant Pat. No. 10,602) |
|---|---|---|
| Ray floret color: | Fades less | Fades more |
| Plant habit: | Shorter/more rounded | Taller/not so rounded |
| Natural season flowering: | 3 weeks earlier | 3 weeks later |

Plant:

*Form, growth and habit.*—Stems upright, freely branching, rounded habit; strong and moderately vigorous growth habit.

*Plant height.*—15-17 cm.
*Plant height (inflorescence included).*—20-23 cm.
*Plant width.*—20-25 cm.
*Garden performance and tolerance to weather.*—Very good.

Roots:
*Number of days to initiate roots.*—10 days at about 22 degrees C.
*Number of days to produce a rooted cutting.*—15-18 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 147A.
*Lower surface.*—Closest to RHS 137B.
*Mature, leaf color, upper surface.*—Closest to RHS 147A.
*Lower surface.*—Closest to RHS 137B.
*Length.*—4-6 cm.
*Width.*—0.8-1.4 cm.
*Shape.*—Narrowly elliptical.
*Base shape.*—Cuneate.
*Apex shape.*—Acute.
*Margin.*—Entire.
*Texture, upper surface.*—Slightly hirsute on margins.
*Lower surface.*—Slightly hirsute on margins.
*Color of veins, upper surface.*—Between RHS 144A and RHS 144B.
*Color of veins, lower surface.*—Between RHS 144A and RHS 144B.

Stem:
*Quantity of main branches per plant.*—About 6-7.
*Color of stem.*—RHS 137A.
*Length of stem.*—About 15.0 cm.
*Diameter.*—0.2-0.3 cm.
*Length of internodes.*—0.5 cm.
*Texture.*—Smooth, glabrous.
*Color of peduncle.*—Slightly lighter than RHS 137A.
*Length of peduncle.*—5.0 cm.
*Peduncle diameter.*—0.1 cm.
*Texture.*—Smooth, glabrous.

Inflorescence:
*Type.*—Compositae type, solitary inflorescences, borne terminally above foliage, ray florets arranged acropetally on a capitulum.
*Natural season flowering.*—Early to mid-September in the north.
*Quantity of inflorescences per plant.*—30-40, plus numerous buds.
*Lastingness of individual blooms on the plant.*—3-4 weeks.
*Fragrance.*—None.

Bud (just when opening/showing color):
*Color.*—RHS 77A.
*Length.*—0.6-0.8 cm.
*Width.*—0.5-0.6 cm.
*Shape.*—Oblate.

Immature inflorescence:
*Diameter.*—2.5 cm.
*Color of ray florets, upper surface.*—Closest to RHS N87A.
*Lower surface.*—Closest to RHS 90C.

Mature inflorescence:
*Diameter.*—3.0-3.5 cm.
*Depth.*—1-1.5 cm.
*Total diameter of 'disc'.*—0.6-0.8 cm.
*Receptacle height.*—0.3 cm.
*Receptacle diameter.*—0.3-0.4 cm.

Ray florets:
*Average quantity of florets.*—About 40-75 in numerous whorls.
*Color of florets, upper surface.*—Closest to RHS N87A, maturing to between RHS N87A and RHS N87B.
*Lower surface.*—Closest to RHS N88D with a darker apex.
*Length.*—1.6-1.8 cm.
*Width.*—0.2-0.25 cm.
*Shape.*—Ligulate to narrowly elliptical.
*Apex shape.*—Rounded and praemorse.
*Margin.*—Entire.
*Texture, upper surface.*—Papillose.
*Lower surface.*—Papillose.

Disc florets:
*Average quantity of florets.*—About 20.
*Color of florets.*—RHS 4C to RHS 4D.
*Length.*—0.6 cm.
*Width.*—0.15 cm.
*Shape.*—Tubular, elongated.
*Apex shape.*—Acute, 5 pointed.

Phyllaries:
*Quantity.*—About 20.
*Color, upper surface.*—Closest to RHS 137A.
*Lower surface.*—RHS 137A.
*Length.*—0.5 cm.
*Width.*—0.1-0.15 cm.
*Shape.*—Lanceolate.
*Apex shape.*—Acute.
*Based.*—Fused.
*Margins.*—Entire.
*Texture, upper surface.*—Smooth.
*Lower surface.*—Hirsute on margins.

Reproductive organs:
*Gynoecium.*—Present on both florets.
*Pistil.*—1.
*Length.*—0.5-0.6 cm.
*Style color.*—RHS 1C but more translucent looking.
*Style length.*—0.4-0.5 cm.
*Stigma color.*—RHS 1B.
*Stigma shape.*—Bi-parted.
*Ovary color.*—Not observed.
*Androecium.*—Present on only disc florets.
*Stamens.*—1.
*Color of filaments.*—RHS 4C.
*Length filaments.*—0.2 cm.
*Anther color.*—RHS 4A.
*Anther length.*—0.1 cm.
*Anther shape.*—Oblong.
*Color of pollen.*—Not observed.
*Pollen amount.*—Not observed.
*Fertility/seed set.*—Has not been observed on this hybrid.

Disease/pest resistance: Disease/pest resistance has not been observed on this hybrid.

What is claimed is:

1. A new and distinct variety of *Aster* plant named 'Synbul Henfirst' substantially as illustrated and described herein.

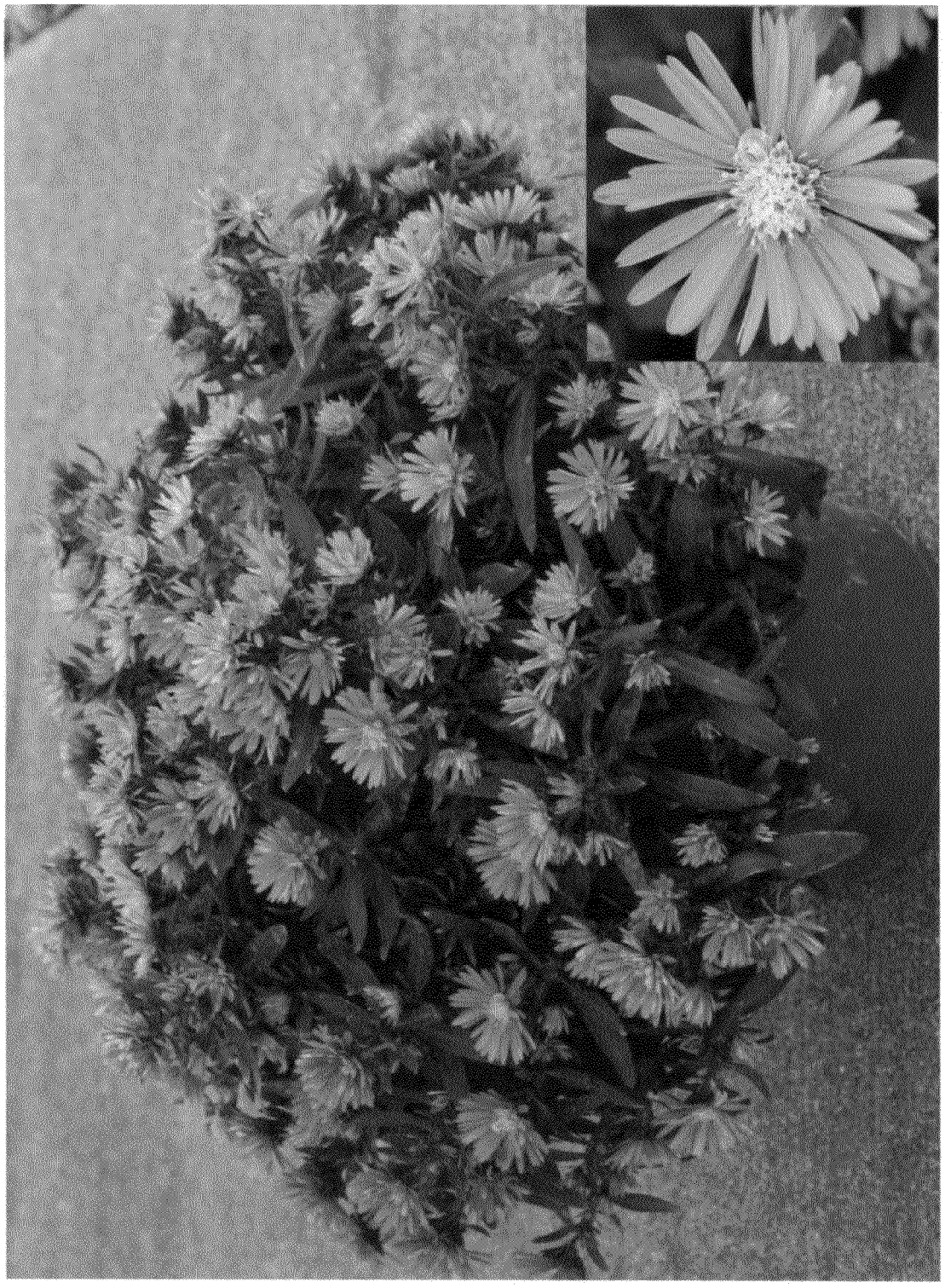

* * * * *